United States Patent [19]

Block et al.

[11] Patent Number: 4,909,990

[45] Date of Patent: Mar. 20, 1990

[54] IMMUNOASSAY APPARATUS

[75] Inventors: Myron J. Block, 334 N. Salem St., North Salem, N.H. 03073; Steve J. Lackie, Malden; Thomas R. Glass, Watertown, both of Mass.

[73] Assignee: Myron J. Block, North Salem, N.H.

[21] Appl. No.: 92,177

[22] Filed: Sep. 2, 1987

[51] Int. Cl.$^4$ .................. G01N 21/63; G01N 21/51; G01N 21/15

[52] U.S. Cl. .................. 422/82.11; 435/291; 435/808; 436/805; 436/807; 436/827; 422/82.08; 422/82.05

[58] Field of Search .............. 422/68; 436/805, 807, 436/827; 435/808, 291

[56] References Cited

U.S. PATENT DOCUMENTS

| | | | |
|---|---|---|---|
| 4,447,546 | 5/1984 | Hirschfeld | 436/527 |
| 4,577,109 | 3/1986 | Hirschfeld | 422/68 |
| 4,608,344 | 8/1986 | Carter et al. | 422/68 |
| 4,666,672 | 5/1987 | Miller et al. | 422/68 |
| 4,671,938 | 6/1987 | Cook | 436/805 |
| 4,810,658 | 3/1989 | Shanks et al. | 422/68 |
| 4,844,869 | 7/1989 | Glass | 422/68 |

FOREIGN PATENT DOCUMENTS

81/00912  4/1981  World Int. Prop. O. .......... 422/68

Primary Examiner—Christine M. Nucker
Attorney, Agent, or Firm—Schiller, Pandiscio & Kusmer

[57] ABSTRACT

An assay apparatus employing total internal reflection of excitation radiation at the interface between a replaceable optically conductive rod or fiber and a surrounding liquid phase of lower index of refraction. Immobilized on the surface of the fiber is a component of a complex formed in an immunological-type specific reaction. A fluorophore that can be excited into fluorescence by the excitation radiation is attached to another component of the complex. The rod is coaxially mounted within a tube that is sized with respect to said rod so that a fluid sample may be introduced into said tube.

The rod and tubing are supported in a mounting assembly that is attachable to an optical assembly for transmitting excitation radiation into the proximal end of the rod and receiving fluorescent radiation emitted from the proximal end of the rod. Included in the apparatus is a mounting assembly for centering the rod within tube and for biasing the rod in a first direction against an annular seat. The latter is designed to support one end of the rod so that none of the radiation introduced into the rod is intercepted by the seat. The apparatus also includes a seal arrangement for preventing a fluid sample from escaping from the tube. Additionally, a tapered fiber may be included in the optical system of the assay apparatus for increasing the power and numerical aperture of radiation input into the optical rod.

32 Claims, 8 Drawing Sheets

IMMUNOASSAY APPARATUS

This invention relates to optical apparatus for carrying out chemical and biochemical assays, and more particularly to an improved fiber optics apparatus for such assays.

Among the large variety of chemical and biochemical equipment used for analysis or assay, is an optical system employing the principles of attenuated total internal reflection (ATR) spectroscopy. Particularly useful for immunoassays, such an optical system employs an optical fiber or rod upon a portion of the outer surface of which an antibody is covalently immobilized, adsorbed or the like. The antibody is selected to be reactive with an antigen in a solution to be assayed or tested. A light beam introduced into one end of the optical rod will be totally internally reflected in the dense medium of the rod, and will generate in the rarer medium or test solution an electromagnetic waveform, known as the evanescent wave component. The latter, for practical purposes, characteristically effectively extends only a fraction of a wavelength across the interface between the rod and test solution. This penetration, however, is sufficient to permit substantial optical interaction between the evanescent wave component and the immobilized antibody with which the antigen in the test solution will complex, and only minimally with any bulk solution in which the antigen was present. Such optical interaction then permits one to assay the antigen. A number of such systems using internal total reflection spectroscopy for an assay are known and have been described, for example, in U.S. Pat. Nos. 4,133,639 in which is disclosed a system based on absorption of the evanescent wave by the analyte; and 4,321,057 and 4,399,099 both of which disclose systems that detect changes in the radiation transmitted through the fiber; 4,447,546 which describes a fluorescence immunoassay system; and others.

An immunoassay apparatus developed by T. Hirschfeld (U.S. Pat. No. 4,447,546 issued May 8, 1984) employs total internal reflection at an interface between a solid phase and a fluid phase of lower index of refraction to produce an evanescent wave in the fluid phase. Fluorescence excited by the wave is observed at angles greater than the critical angle, by total reflection within the solid medium. The solid phase is arranged and illuminated to provide multiple total internal reflections at the interface.

Typically, the solid phase is in the form of an optical fiber or rod to which is immobilized a component of a complex formed in an immunochemical reaction. A fluorophore is attached to another component of the complex. The fluorescent labeled component may be either the complement to or the analog of the immobilized component, depending upon whether competitive or sandwich assays are to be performed. In the case of competitive assays, the labeled component is typically preloaded to the immobilized component in a controlled concentration.

The fiber and the attached constituent of the assay are immersed in a fluid phase sample and the exciting illumination is injected into an input end of the fiber. The evanescent wave is used to excite fluorescence in the fluid phase, and that fluorescence which tunnels back into the solid phase (propagating in directions greater than the critical angle) is detected at the input end of the fiber.

The observed volume of sample is restricted not only by the rapid decay of the evanescent wave as a function of distance from the interface, but by an equally fast decrease, with distance, of the efficiency of tunneling; the more distant fluorophores not only are less intensely excited and thus fluoresce less, but their radiation is less efficiently coupled into the fiber. Consequently, the effective depth of the sensed layer is much reduced compared to the zone observed by total reflection fluorescence alone, the coupling efficiency effectively scaling down the zone.

Multiple total internal reflections in the solid phase allow the illuminating beam to excite repeatedly an evanescent wave, thereby more efficiently coupling the small excitation source to the sample volume. This also increases the amount of sample sensed. The latter is also enhanced by diffusive circulation of the sample past the fiber surface and to which the material being assayed adheres by reaction as it passes. Diffusion makes the actually sampled layer thickness much larger than the thin surface layer that is all that contributes to the background.

All of the radiation that tunnels back into the fiber within the total reflection angle is thus trapped within the fiber. The power available from the fluorescence increases with the length of fiber within the fluorescing material. However, the optical throughput of the system (determined by the diameter and the numerical aperture of the fiber) remains constant. The total fluorescent signal coming from the entire surface of the fiber, multiplied by the increase in sample volume due to diffusion, thus becomes available in a very bright spot (that is the cross-section of the fiber in diameter) exiting the fiber at its input end through a restricted angle determined by the critical angle of reflection within the fiber. Such signal is easily collected at high efficiency and throughput matched to a small detector.

For excitation radiation initially propagating through an optical fiber of refractive index $n_0$, otherwise surrounded by a material of refractive index $n_1$, the maximum acceptance angle B of input radiation into the fiber can be found from the equation:

$$NA = n_2 \sin b = \sin b = (n_0^2 - n_1^2)$$

where $n_2$ is the refractive index of the medium (typically air) through which the radiation is initially propagated so as to be incident upon an end of the fiber, and NA is the so-called numerical aperture of the fiber. The maximum acceptance angle B is simply defined as:

$$B = \sin^{-1} NA \qquad (2)$$

and B=b when $n_2=1$ (e.g. $n_2$ is for dry air). Thus, the numerical aperture for a fiber is highest when the fiber core material has a very high index and the medium surrounding it has a very low index, or $n_0 >> n_1$. For example, satisfactory sensitivities can be obtained where a transparent fiber (glass, silica, polymer or the like) of ordinary index of refraction is surrounded by an aqueous solution that typically has an index of refraction in the vicinity of 1.33–1.35.

In known immunoassay apparatus, such as the one described in the aforementioned U.S. Pat. No. 4447546 to Hirschfeld, an optical fiber is supported within a capillary tube in approximately co-axial alignment therewith. A fluid sample is introduced into the space formed between the fiber and the tube and is drawn into and supported in the space by capillary action. To maximize sensitivity and efficiency of such an immunoassay apparatus, it is important that the fiber remain substantially coaxially centered within the capillary tube. If the fiber contacts the capillary wall, capillary action may be adversely affected, and total internal reflection may not be achieved since radiation may pass out of the fiber at the point of contact between the fiber and the capillary wall. Loss of sensitivity typically occurs in the apparatus as a result of such refraction.

Inasmuch as the intensity of the fluorescent signal tunnelling back into the fiber is proportional to a very high power (ca. 9th) of the numerical aperture (as defined in part by the refractive index of the sample in which fluorescence is excited), it is important to try to preserve the maximum possible numerical aperture throughout the system.

It is also important that the proximal end of the fiber into which optical radiation is transmitted and from which fluorescent radiation is emitted be supported in a fixed axial position with respect to the means for transmitting optical radiation into the fiber. In the event the proximal end of the fiber does not lie at a fixed position with respect to the objective lens of the optical system associated with the immunoassay apparatus, the amount and orientation of transmitted radiation entering the rod may vary. This variation may adversely affect the accuracy and sensitivity of the apparatus.

At least two techniques have been developed in known immunoassay apparatus for locating an optical fiber within a capillary tube. The first technique involves supporting the fiber in cantilever fashion at its distal end, i.e. the end opposite the end where optical radiation is transmitted into said fiber. The proximal end of an optical fiber supported by this technique is displaceable both axially and radially. Such displacement gives rise to the aforementioned loss of instrument sensitivity.

In the second technique, the proximal end of the optical fiber is supported using a conventional fiber optic connector. Use of these connectors typically involves covering the outer surface of the fiber adjacent its proximal end with a cladding material typically consisting of a transparent high molecular weight polymer. Known cladding materials typically have a refractive index higher than that of the sample, e.g. 1.40 to 1.45, with the result that the numerical aperture of the fiber is reduced to a level at which acceptable sensitivity levels cannot readily be achieved with the apparatus.

The evanescent zone tends to increase in depth and the sensitivity of the system also increases as the numerical aperture of the fiber increases. Thus, it is preferred that the numerical aperture of the system be maximized. Such maximization has heretofore been limited by the second of the above-described techniques used to clamp and support the fiber.

Fiber-optic assay systems having a disposable optical fiber assembly are useful in testing for the presence of harmful viruses. The optical fiber assembly that receives the fluid sample containing the potentially harmful viruses is readily disposable. Thus, to improve the efficiency and reduce the cost of such important and widely-used assay procedures, it is important that the fiber-optic assembly of the assay system be easily replaceable and have a high numerical aperture.

A principal object of the present invention is therefore to provide an improved fiber-optic assay system employing an optical rod or fiber positioned within and spaced from an enclosure, which system comprises means for mounting the rod within the enclosure so that the rod is positioned and supported in a fashion maximizing the sensitivity of the system. Other objects of the present invention are to provide such a system in which the rod and enclosure may be readily inserted into and removed from a base assembly in which the optics of the system are located, with the rod being firmly supported and properly optically aligned automatically upon the insertion of the rod into the base; and to provide such a system in which the numerical aperture of the rod is maximized by supporting the rod in alignment with the optics of the system such that substantially none of the input optical radiation intersects the mounting assembly for supporting the proximal end of the rod; to provide an assay system designed to prevent a fluid assay sample contained within the enclosure from escaping from the enclosure and the base assembly for supporting the enclosure; and to include in the optical system of the present invention a tapered fiber for increasing the power and numerical aperture of radiation input into the optical fiber.

The foregoing and other objects of the present invention are achieved by an assay system comprising an optical rod or fiber positioned within an enclosure, and a base assembly including a holder for receiving the proximal ends of the rod and enclosure. The holder comprises a concave aperture that tapers frusto-conically to a bore having a seat formed therein for supporting the proximal end of the fiber. The seat may be designed to block input radiation intersecting the radially-outermost portions of the proximal end of the fiber so as to eliminate stray light production arising from edge defects in the rod. The holder also has a sleeve portion for supporting and releasably locking the proximal end of the enclosure. A centering device is attached to the distal end of the rod for ensuring the rod remains substantially centered within the enclosure. The centering device is designed to permit a fluid sample to be introduced into the enclosure at the distal end thereof. A spring is attached to the distal end of rod, preferably via the centering device, and the enclosure for urging the rod into engagement with the seat in the holder. In alternative embodiments of the invention, seal means are provided in the base assembly and at the distal end of the enclosure for preventing an assay sample disposed within the enclosure from escaping from the enclosure. In another alternate embodiment of the invention the optical system thereof includes a tapered fiber interposed between the optical fiber and the radiation source of the optical system for increasing the power of the radiation input into the optical fiber.

Other objects of the present invention will in part be obvious and will in part appear hereinafter.

The invention accordingly comprises the apparatus possessing the construction, combination of elements and arrangement of parts which are exemplified in the following detailed disclosure, and the scope of the application of which will be indicated in the claims.

For a fuller understanding of the nature and objects of the present invention, reference should be had to the following detailed description taken in connection with the accompanying drawings in which like numerals in the several drawings are employed to denote like parts, and wherein.

Figure 1:
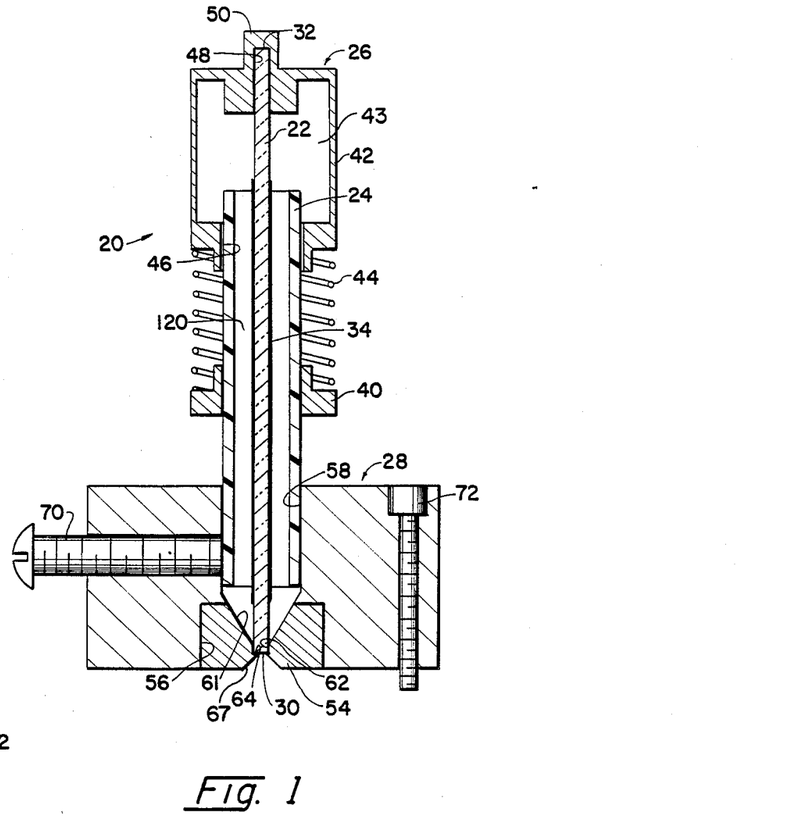
FIG. 1 shows, in idealized, enlarged, longitudinal cross-section, a fiber optic system embodying the principles of the present invention.
Figure 2:
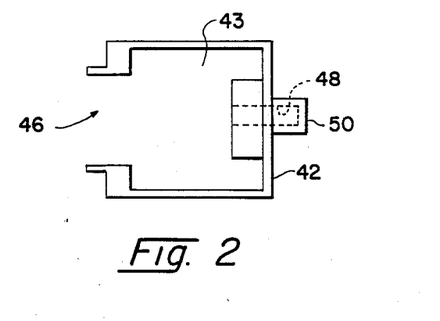
FIG. 2 is a side elevation view of the slidable spider portion of the embodiment illustrated in FIG. 1.
Figure 4:
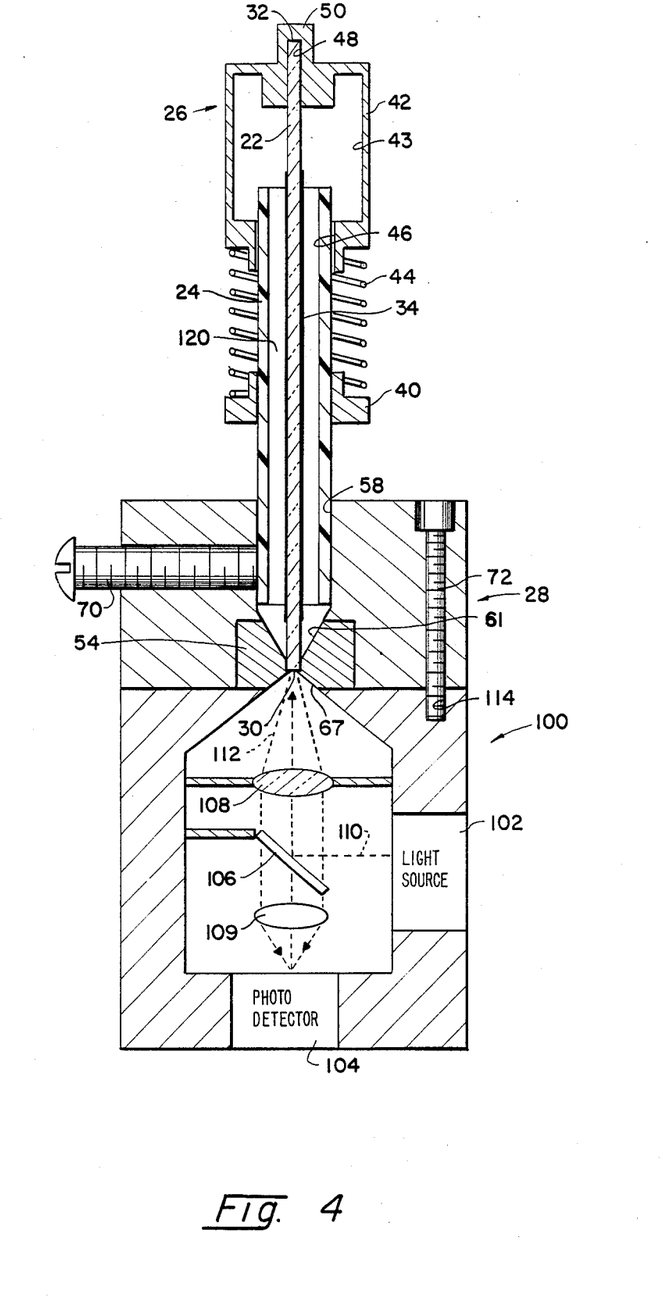
FIG. 4 is an idealized, longitudinal cross-sectional view of the fiber optic system of FIG. 1 and the optical system with which it is adapted to be used.

Referring to FIGS. 1, 2 and 4, there is shown exemplary apparatus 20 for assaying a fluid sample, which apparatus incorporates the principles of the present invention. Apparatus 20 includes optical rod or fiber 22, hollow, elongated enclosure 24, fiber centering device 26 and base member 28, and is similar in many respects to the system shown in the aforesaid U.S. Pat. No. 4,447,546.

Rod 22 is an elongated body extending from its proximal end or entrance face 30 to a distal or terminal end 32. Rod 22 preferably has a substantially circular cross-section. At proximal face 30 the rod surface typically is planar, is disposed normally to the longitudinal axis of the fiber and is preferably highly polished to minimize any blemishes or surface defects that would tend to scatter incident and emitted radiation. Alternatively, proximal face 30 of the rod may be configured in other desired optical shapes to serve, for example, as a magnifying or matching optical surface.

In a preferred embodiment, in which the fluorescence induced at the fiber surface by excitation radiation launched down the fiber is collected or observed at the same proximal end of the fiber at which the excitation radiation is injected, it is desired to prevent stray radiation from going back up the fiber from distal face 32 to proximal face 30. Consequently, face 32 may be shaped to spill out light incident thereon internally, but preferably is coated with a material matching the index of refraction of the medium surrounding face 32, such material being both non-fluorescent and absorbent with respect to the excitation radiation. Typically, an epoxy resin loaded with carbon black serves such function.

Rod 22 is adapted to propagate along its length, by multiple total internal reflection, optical excitation radiation entering proximal face 30 within a conical acceptance angle (B) substantially symmetric with the long axis of the fiber and defined herein before, as well known to those skilled in the fiber optics art, in equation (1). Rod 22 may be any of a very large number of substantially homogeneously materials optically transparent to the excitation radiation, e.g. glassy materials such as glass, crystalline materials such as quartz, sapphire and the like; synthetic polymers such as polyolefins, polypropylenes and the like, and is preferably relatively stiff. Where rod 22 is to be used in fluid assays as described hereinafter, he index of refraction ($n_0$) of the material forming rod 22 must be greater than $n_1$, the index of refraction of the fluid being assayed. The latter index is typically about 1.3 for an aqueous solution. For purposes of an immunoassay apparatus, rod 22 has a length ranging from 3cm to 5cm, with about 4cm being the preferred length. Rod 22 typically has a diameter in the range of from about 0.5mm to 1.5mm, with about 1 mm being the preferred diameter. It should be understood, however, that such length and diameter are merely exemplary and not limiting.

In an exemplary embodiment, it is intended that the operative portion of the fiber surface be defined by the dimensions of an activated region at which the assay is to be performed. To activate the surface of the operative portion of rod 22, the latter is typically treated to provide coating 34 such as is described in detail in U.S. Pat. No. 4,447,546 and is incorporated herein by reference.

Enclosure 24 is preferably but not necessarily optically transparent, and is formed of a material that is relatively insoluble and chemically non-reactive with the fluid being assayed. Typically, enclosure 24 is simply a glass tube having an inside diameter greater than the maximum outside diameter of fiber 22, and preferably dimensioned to delimit a predetermined volume surrounding at least activated coating 34 on fiber 22. In a preferred embodiment, the interspace between the coated surface of fiber 22 and the inside wall of enclosure 24 is of capillary dimension.

Fiber centering device 26 comprises fixed spring mount 40, slidable spider 42 and tension spring 44. Spring mount 40 is secured to the outer surface of tube 24, as by adhesive bonding or other suitable process. Spring mount 40 comprises a relatively rigid, radially-extending element to which one end of tension spring 44 may be attached. As skilled practitioners will appreciate, spring mount 40 may take a variety of forms, including, for instance, an annulus having an outside diameter sized to frictionally engage the interior of tension spring 44. Alternatively, a slot may be formed in spring mount 40 for retaining the one end of tension spring 44.

Slidable spider 42 comprises a hollow body having at least one opening 43 formed in a sidewall thereof into which a fluid sample may be introduced. An exemplary spider 42 having a substantially rectangular shape and opposed side openings 43 is shown in FIG. 2. Aperture 46 is formed in one end of spider 42, with the inside diameter of the aperture being slightly greater than the outside diameter of tube 24 so that tube 24 is slidably receivable in aperture 46. In this position, spider 42 is substantially coaxially centered on tube 24. At an opposite end of spider 42, blind bore 48 is formed in enlarged portion 50 of the spider. The inside diameter of bore 48 is selected so that the distal end of rod 22 may be secured in the bore by force fit or adhesive bonding. Enlarged portion 50 may be formed integrally with spider 42 or may comprise a separate element that is press-fitted into an appropriate aperture provided in the end of spider 42 opposite opening 46. In any case, the longitudinal axis of bore 48 must substantially coincide with the longitudinal axis of aperture 46. An opposite end of tension spring 44 is secured to spider 42 adjacent aperture 46 by suitable means, such as adhesive bonding or inserting the opposite end of the spring into a spring retaining slot (not shown) formed in the spider 42.

Tension spring 44 is preferably a coil spring having a suitable length and spring coefficient. As described more fully hereinafter the length and spring coefficient of spring 44 and length of rod 22 are selected so that proximal end 30 protrudes a selected distance from tube 24 when spring 44 is unbiased. The spring coefficient of spring 44 is further selected so that rod 22 may be suitably biased with respect to tube 24, as described more fully hereinafter.

Figure 3:
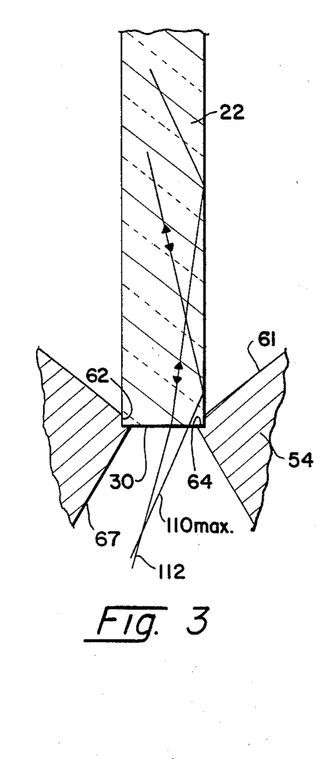
FIG. 3 is an idealized, enlarged, fragmentary, longitudinal cross-sectional view, of a portion of the embodiment illustrated in FIG. 1.

Referring now to FIGS. 3 and 4, base member 28 is made from a block of relatively rigid material such as aluminum or a dense synthetic polymer. A hard insert 54, made typically from stainless steel, titanium or the like, is disposed in a cavity 56 formed at a central location on the bottom surface of base member 28. An aperture extends through member 28 that comprises large diameter portion 58 that terminates in frusto-conically tapering portion 61 that tapers to reduced diameter portion 62. The latter terminates in a radially-inwardly extending annular seat 64 having an inside diameter that is a selected amount less than the outside diameter of rod 22, as described more fully hereinafter. Thus, the opening defined by seat 64 and reduced diameter portion 62 provide a bore and counterbore, respectively, in the apex end of frusto-conically tapering portion 61. A second frusto-conical portion 67 opens outwardly from seat 64 toward the bottom surface of base member 28. Preferably, at least portion 62, seat 64, and frusto-conical portions 61 and 67 are disposed in insert 54.

The inside diameter of large diameter portion 58 is slightly greater than the outside diameter of tube 24 so that the latter may be slidably disposed in the large diameter portion. Similarly, the inside diameter of reduced diameter portion 62 is slightly greater than the outside diameter of rod 22 so that the latter may be slidably disposed in the reduced diameter portion. Seat 64 is sized to engage only the radially-outermost portion of proximal end 30 when rod 22 is inserted in reduced diameter portion 62, so as to achieve maximum sensitivity in the apparatus, as described hereinafter.

Base member 28 comprises means for securing tube 24 into portion 58, such as set screw 70. Additionally, as described more fully hereinafter, means are provided in base member 28, such as allen screw 72, for securing the base member to the optical system with which the assay apparatus 20 is adapted for use.

Referring now to FIG. 4, the present assay apparatus 20 is designed for use with an optical system 100 comprising light source 102, photo detector 104, beam splitter 106, objective lens 108 and secondary lens 109. The foregoing elements of optical system 100 are disposed in fixed optical relationship to one another and to immunossay apparatus 20, as described more fully hereinafter. By this relationship, light beam 110 generated by light source 102 is folded by beam splitter 106 so as to pass through objective lens 108 and into rod 22 through proximal end 30. Light source 102, beam splitter 106, objective lens 108 and secondary lens 109 are selected and operated so that substantially all the rays of beam 110 intersect proximal end 30 at less than or equal to the maximum acceptance angle at end 30. Of course, other optical elements may be used in place of objective lens 108 for imaging the beam of input radiation, such as an optical fiber.

Any light beams 112, the latter consisting of fluorescence excited by the evanescent wave, emitted from proximal end 30 pass through objective lens 108 through beam splitter 106 and are focused by secondary lens 109 so as to contact photo detector 104. Frusto-conical portion 67 is provided so that light beams 112 are not intercepted by sections of insert 54 as they travel toward objective lens 108.

Threaded aperture 114 may be provided in optical system 100 for receiving Allen screw 72, whereby base 28 may be readily secured to and separated from optical system 100 if desired.

To maximize the accuracy and efficiency of the present assay apparatus 20, it is important that the flat face of proximal end 30 lie at a fixed position with respect to objective lens 108. To this end, insert 54 is formed so that when base member 28 is secured to optical system 100, as shown in FIG. 4, seat 64 is fixed at a preselected focal or axial position with respect to objective lens 108.

In operation of the embodiment of FIGS. 1–4, coating 34 of rod 22 is formed from any of a number of activating reagents (such as a constituent of an antibody-antigen complex that includes a fluorescent tag) and is essentially subjected to the same procedures as are described in U.S. Pat. No. 4,447,546. Rod 22 and tube 24, with centering device 26 affixed thereto, are inserted together into aperture 58 until proximal end 30 engages seat 64. Frusto-conical portion 61 guides rod 22 into coaxial alignment with portion 62 to facilitate the seating of proximal end 30. Preferably, this operation is effected by grasping and pressing down on spring mount 40 until proximal end 0 engages seat 64.

Tube 24 is then inserted farther into aperture 58 so as to bias tension spring 44. Set screw 70 is then tightened to hold tube 24 in fixed position in aperture 58. In this position, spider 42 ensures rod 22 remains substantially coaxially centered within tube 24. The length and spring coefficient of spring 44 and length of rod 22 are selected so that proximal end 30 engages seat 64 before tube 24 contacts frusto-conical portion 61, whereby spring 44 holds proximal end 30 in relatively firm contact with seat 64. Insert 54 is made from a hard material so that proximal end 30 will not scratch or shave off portions of insert 54 during insertion of rod into portion 62.

Next, interspace 120 between enclosure 24 and rod 22 is filled through opening 43, as with a hypodermic syringe or other suitable device, with a liquid sample of the material to be assayed. The sample is held in interspace 120 by the meniscus surfaces formed at opposite ends of enclosure 24. The sample is allowed to incubate in interspace 120 as desired to permit the material being assayed in the fluid sample to diffuse to and react with coat 34 to form the tagged complex.

Referring to FIGS. 3 and 4, light source 102 is then activated to generate light beam 110, the latter being folded at beam splitter 106 so as to intersect proximal end 30 at less than or equal to the maximum acceptance angle at end 30. Objective lens 108 is selected and axially positioned with respect to seat 64 so that the radially outermost rays $110_{max}$ (FIG. 3) of light beam 110 pass just radially inwardly of the radially- innermost portion of seat 64. Consequently, the seat does not intercept any of input light rays 110 and therefore does not adversely affect total internal reflection. By this selection and positioning of objective lens 108, the size of the excitation spot on proximal end 30 is precisely controlled and the creation of errors arising from edge defects on the rod are minimized. Because seat 64 necessarily physically abuts the periphery of end 30, it may serve as a mask to define the size of the excitation spot on the fiber face created by light beam 110 and eliminate errors arising from defects on the edge of end 30.

The length of the reduced diameter portion 62 is selected so that rays 110, including rays $110_{max}$, reflect from the interface of the rod 22 axially distal of where reduced diameter portion 62 engages the rod. Consequently, none of rays 110 intersect reduced diameter portion 62, ensuring no interference with total internal reflection in rod 22.

As light beam 110 reflects down rod 22, it is capable of exciting or inducing fluorescence in coat 34 by an evanescent wave that accompanies the transmission of the beam down the fiber. A portion of the fluorescence induced in the tagged complex at coat 34 then tunnels back into the fiber from the excited material and is transmitted by total internal reflection back out through proximal face 30 as light beam 112. The latter is received by photo detector 104, thereby indicating the presence of a tagged complex at coat 34.

The present invention provides fiber optics assay apparatus with as high a numerical aperture as may be achieved subject to the constraints imposed by the refractive index of the sample and the index of the rod, inasmuch as there is no degradation in numerical aperture due to a contacting, intervening mounting or cladding material between or at the proximal end of the fiber and that portion of the fiber in which fluorescence is excited. Additionally, since rod 22 is held firmly by assay apparatus 20, there is substantially no loss in throughput ($NA^2$ × the exposed surface area of proximal end 30) that might otherwise occur due to movement of the rod. Since one may start with a fairly substantial glass "rod" rather than the fine fibers such as are disclosed in U.S. Pat. No. 4,447,546, one is not limited to the type of glass that may be used, i.e. telecommunication glasses, and therefore one may use very high index glasses, crystals, polymers and the like, which further enhances the maximum numerical aperture that can be obtained at the fiber portion in contact with the sample.

Figure 5:
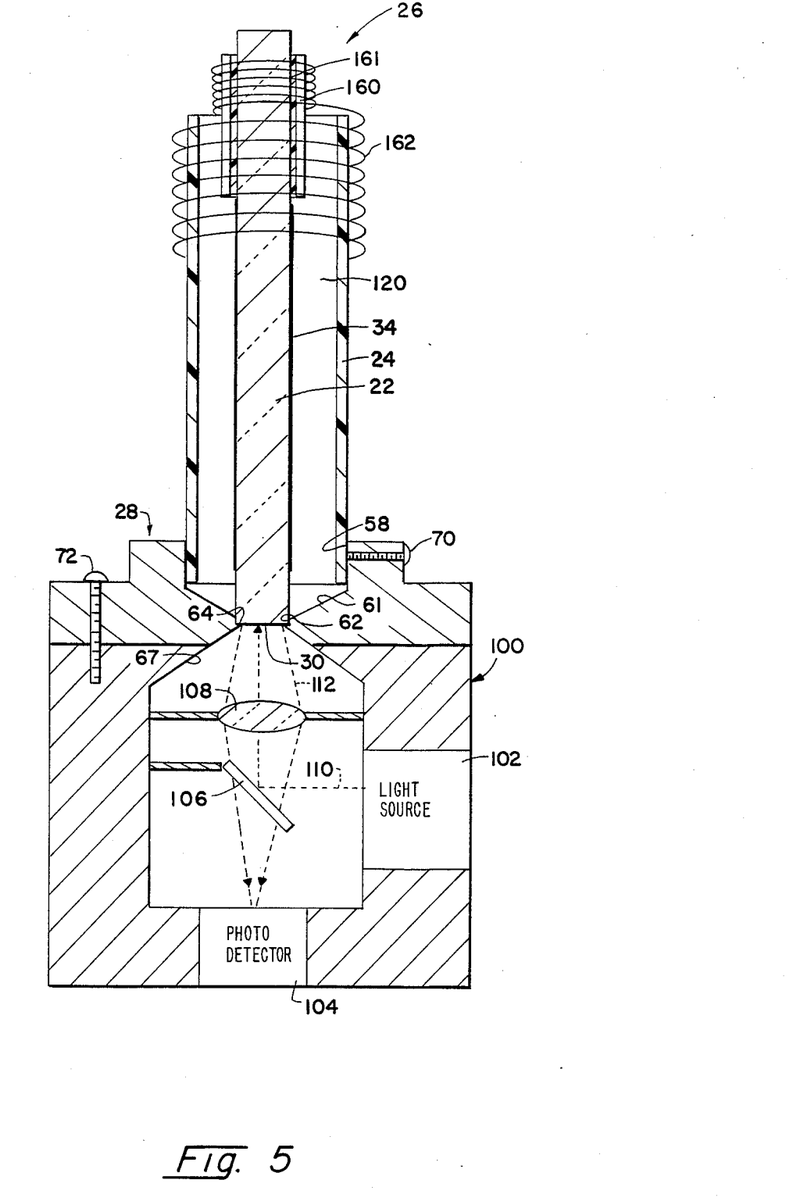
FIG. 5 is an idealized longitudinal cross-sectional view of a fiber optic system embodying the principles of another embodiment of the present invention and an optical system with which it is adapted to be used.

Referring now to the embodiment of FIG. 5, another assay apparatus is shown comprising rod 22, tube 24, centering device 26 and base assembly 28. Rod 22, tube 24, and base assembly 28 are substantially identical to the rod, tube and base assembly of the embodiment shown in FIG. 1. As described hereinafter, centering device 26 varies somewhat from the centering device of the embodiment shown in FIG. 1. Like the embodiment of FIG. 1, base assembly 28 is attachable to an optical system 100 comprising light source 102, photo detector 104, beam splitter 106 and objective lens 108. The assay apparatus shown in FIG. 5 is constructed so that (a) proximal end 30 of rod 22 lies at a fixed focus with respect to objective lens 108, (b) rod 22 is substantially centered in tube 24, and (c) rod 22 is prevented from moving axially or radially relative to its length.

To these ends, centering device 26 is provided comprising spacer 160 secured to rod 22 adjacent the distal end thereof by adhesive 161. The thickness of spacer 160 is less than that of interspace 120 so that the spacer may be received in interspace 120 while at the same time providing an opening adjacent thereto through which a fluid assay sample may be dispensed into interspace 120. The length of spacer 160 is selected so that when rod 22 and tube 24 are secured to base assembly 28, as shown in FIG. 5, at least a portion of the spacer is surrounded by tube 24. Spacer 160 may have any one of a variety of different configurations, the only requirement being that the foregoing length and thicknesses parameters be achieved. Exemplary configurations for spacer 160 include a pair of rectangular elements secured to rod 22 in diametrically opposed relationship to one another or a cylindrical element, such as a segment of a conventional capillary tube.

Centering device 26 also comprises a coil spring 162 made of a material (e.g. stainless steel, dense synthetic polymers, or other suitable materials) that is substantially nonreactive with fluids to be assayed in the present device. One end of spring 162 surrounds and is secured preferably to spacer 160, and the other end of spring 162 surrounds and is secured to tube 24. Spring 162 may be secured to spacer 160 and tube 24 by sizing the spring so that it compressively engages the spacer and tube. Alternatively, the ends of spring 162 may be bonded, as by suitable adhesive, to spacer 160 and tube 24. Like the embodiment of FIG. 1, the length and spring coefficient of spring 162 and length of rod 22 are selected so that proximal end 30 is disposed within or only protrudes a selected distance from tube 24 when spring 162 is unbiased. The spring coefficient of spring 162 is further selected so that rod 22 may be suitably biased with respect to tube 24, as described more fully hereinafter.

Base member 28 is substantially identical to the base member of the embodiment or FIG. 1 and thus comprises large diameter portion 58, frusto-conical portion 61, reduced diameter portion 62, seat 64 and frusto-conical portion 67. Portion 58 is sized to slidably receive tube 24 and portion 62 is sized to slidably receive rod 22. Base member 28 is constructed so that proximal end 30, when seated in seat 64, lies at a fixed position with respect to objective lens 108.

The entire member 28 is made of a hard material such as stainless steel, titanium and the like so that rod 22 will not scratch or shave off pieces of reduced diameter portion 62 during insertion of the rod in the reduced diameter portion. Alternatively, base member 28 may be made from a softer, yet rigid material such as aluminum, and an insert (not shown) made from a hard material such as stainless steel, such as insert 54 of the FIG. 1 embodiment, may be used in the region of the base member where portions 61 and 62 and seat 64 are formed. Means such as a set screw 70, is provided in base member 28 for securing tube 24 within aperture portion 58, and means such as a set screw 72, may be provided for securing base member 28 to optical system 100.

The operation of the embodiment of FIG. 5 is substantially identical to the operation of the embodiment of FIGS. 1–4. Rod 22 and tube 24, with centering device 26 affixed thereto, are inserted together into aperture 58 until proximal end 30 engages seat 64. Frusto-conical portion 61 guides rod 22 toward portion 62. Preferably this operation is effected by grasping tube 24 and sliding it into aperture 58 until proximal end 30 engages seat 64.

Continued motion of tube 24 in the same direction tensions spring 162 which serves to keep end 30 in engagement with seat 64. Set screw 70 is then tightened to hold tube 24 in fixed position in aperture 58. In this position, spacer 160 ensures rod 22 remains substantially centered within tube 24, and spring 162 urges proximal end 30 into engagement with seat 64.

Next, interspace 120 between enclosure 24 and rod 22 is filled through the gap between enclosure 24 and spacer 160, as with a hypodermic syringe or other suitable device, with a liquid sample of the material to be assayed. The sample is held in interspace 120 by the meniscus surfaces formed at opposite ends of enclosure 24. The sample is allowed to incubate in interspace 120 as desired to permit the material being assayed in the fluid sample to diffuse to and react with coat 34 to form the tagged complex.

Light source 102 is then activated to generate light beam 110, the latter being folded at beam splitter 106 so as to intersect proximal end 30. Objective lens 108 is selected and axially positioned with respect to seat 64 so that seat 64 does not intercept any of the input light rays 110 and therefore does not adversely affect total internal reflection. As light beam 110 reflects down rod 22, the beam is capable of exciting or inducing fluorescence in coat 34 by an evanescent wave that accompanies the transmission of the beam down the fiber. A portion of the fluorescence induced in the tagged complex at coat 34 then tunnels back into the fiber from the excited material and is reflected back out through proximal face 30 as light beam 112. The latter is received by photodetector 104, thereby indicating the presence of a tagged complex at coat 34.

Figure 6:
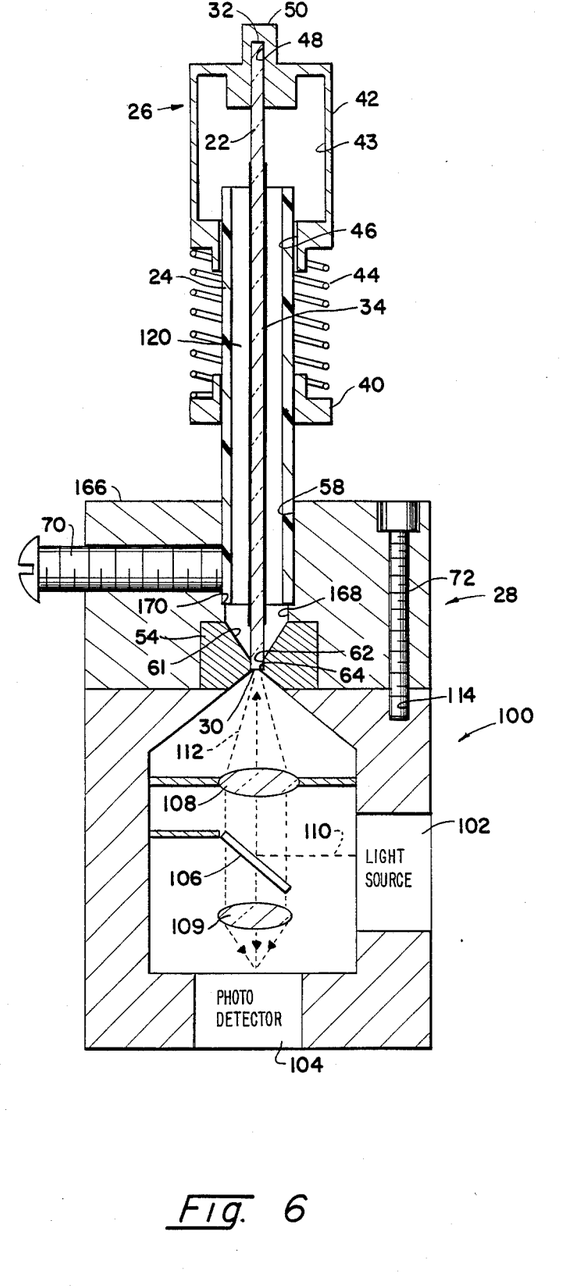
FIG. 6 is an idealized longitudinal cross-sectional view of a fiber optic system embodying the principles of still another embodiment of the present invention and an optical system with which it is adapted to be used.

An alternative embodiment of the assay apparatus shown in FIGS. 1-4 is illustrated in FIG. 6. The embodiment of FIG. 6 is substantially identical to the embodiment illustrated in FIGS. 1-4, except that base member 28 has been modified so as to substantially prevent an assay sample disposed within tube 24 from leaking out of the tube and escaping past proximal end 30 of rod 22 or out of portion 58 past the junction of large diameter portion 58 and top surface 166 (FIG. 6) of base member 28.

In most applications of the present invention, menisci will form at opposite ends of a fluid assay sample disposed within tube 24. As noted above, these menisci provide a barrier that prevents the fluid sample from leaking out of tube 24. As menisci typically do not have the strength to oppose forces much greater than the force of gravity, in certain applications of the present invention smooth, barrier-forming menisci will not form, or will break apart into irregular menisci portions shortly after formation. For instance, if the assay sample is injected into and maintained within tube 24 under pressure, or if the assay apparatus is used in an environment subject to frequent and large vibrations, these greater forces may be encountered thereby causing the breakup of smooth, barrier-forming menisci.

In the alternative embodiment illustrated in FIG. 6, a reduced diameter portion 168 is provided in large diameter portion 58 at the junction of the latter with frusto-conically tapering portion 61. The diameter of portion 168 is selected so that a radially-extending seat or lip 170 is defined at the junction of portion 168 and portion 58. Seat 170 is sized and configured so that (1) when the proximal end of tube 24 is positioned within portion 58 so as to engage seat 170, and (2) when the tube is secured within portion 58 by set screw means 70, an assay sample disposed within tube 24 is prevented from leaking out of the proximal end of the tube and passing along the outer surface of the tube toward the junction of top surface 166 and portion 58. Typically, seat 170 extends normally to the longitudinal axis of tube 24, although the seat may be configured to extend transversely to the longitudinal axis of the tube.

Figure 6A:
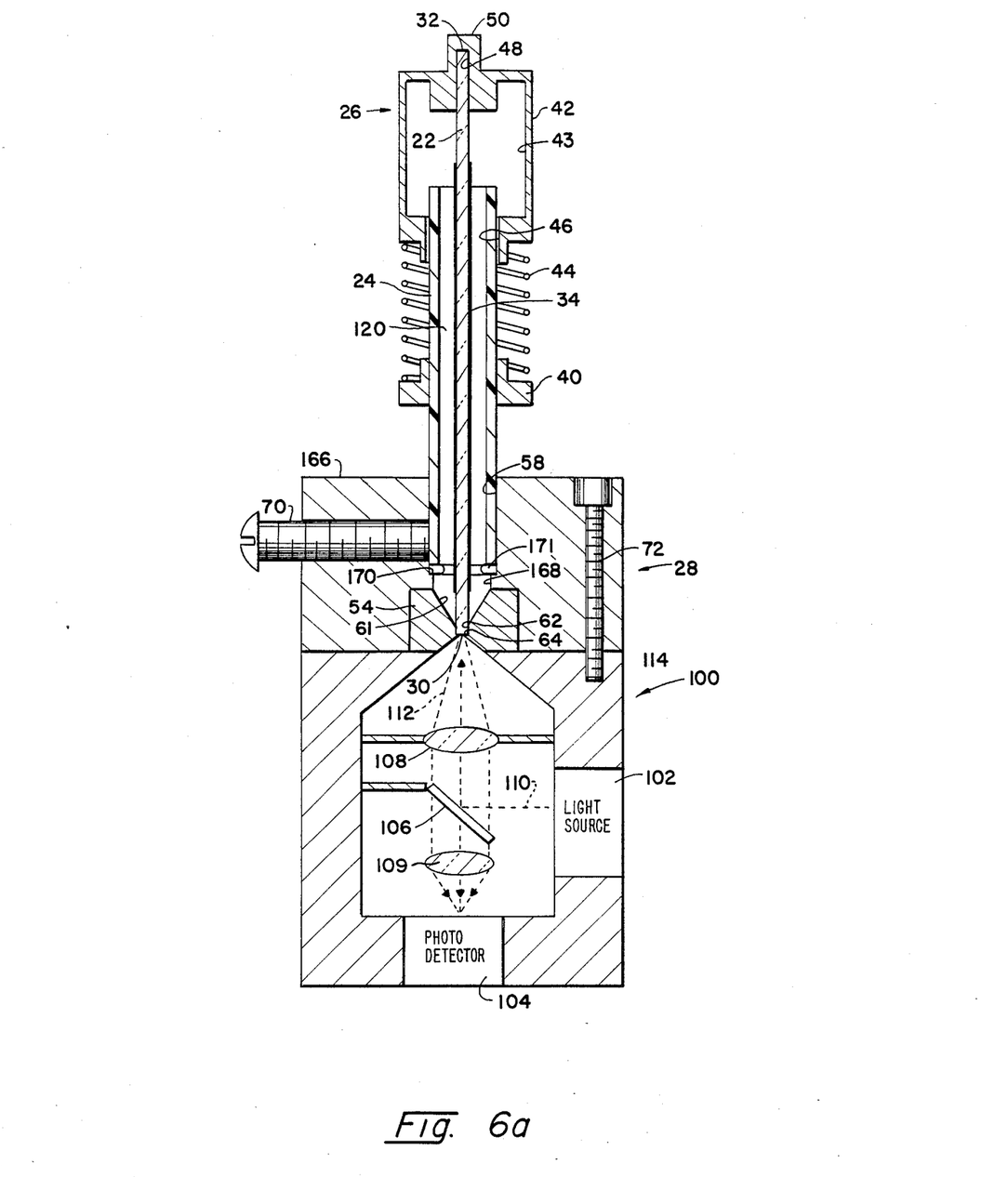
FIG. 6a is identical to FIG. 6, except that a seal is shown positioned between the proximal end of the tube and the base.

Alternatively, seat 170 may be formed at the junction of portion 58 and frusto-conically tapering portion 61. In this alternative arrangement, reduced diameter portion 168 is eliminated. Referring to FIG. 6a, optionally, an elastomeric O-ring 171 or other suitable means may be disposed at seat 170 to ensure a fluid-tight seal is achieved between base member 28 and the proximal end of capillary tube 24.

Figure 6B:
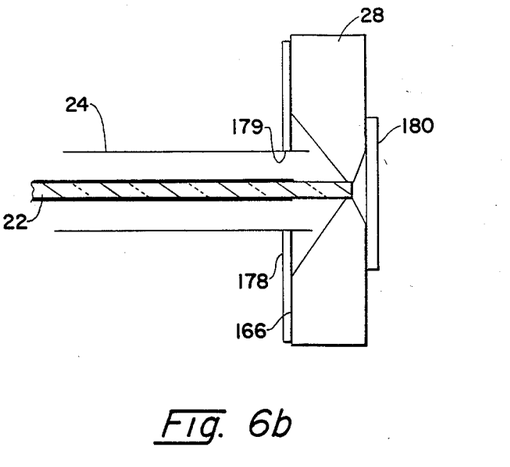
FIG. 6b is a fragment of an embodiment such as in FIG. 6, but shows additional seals between the tube and base member.

The fragment shown in FIG. 6b, limited to the volume of the joint between tube 24 and base member 28 (like numerals denoting like parts), includes gasket 178, preferably a disk of elastic material having central aperture 179. The latter aperture is slightly smaller in diameter than the outside diameter of tube 24. Aperture 179 is coaxially disposed with respect to portion 62 of member 28 immediately adjacent and in contact with or adhered to surface 166 of member 28; thus the gasket will tightly surround tube 24 when the latter is emplaced in the aperture 179. By installing gasket 178 on surface 166 prior to insertion of tube in aperture 179, the gasket not only subsequently serves as a seal between tube 24 and member 28, but provides automatic alignment and support for the tube. Also, because the junction of proximal face 30 of rod 22 with seat 64 may not provide an acceptable seal under many circumstances, it may be desirable to cement an optically transparent and preferably flat plate 180, typically of glass, across frusto-conical portion 67 so as to create an airtight chamber between plate 180 and proximal face 30 of rod 22.

As with the embodiment illustrated in FIGS. 1-4 reduced diameter portion 62 (FIG. 6) has a diameter that is slightly larger than the outside diameter of rod 22, and seat 64 (FIG. 6) is sized to engage the radially-outermost portion of rod end face 30. By this configuration, when rod 22 is disposed to engage seat 64, an assay sample disposed in tube interspace 120 is substantially prevented from escaping past rod proximal end 30. Fiber centering device 26 is provided to bias rod 22 axially toward seat 64, so as to ensure the proximal end 30 remains engaged with seat 64.

Figure 7:
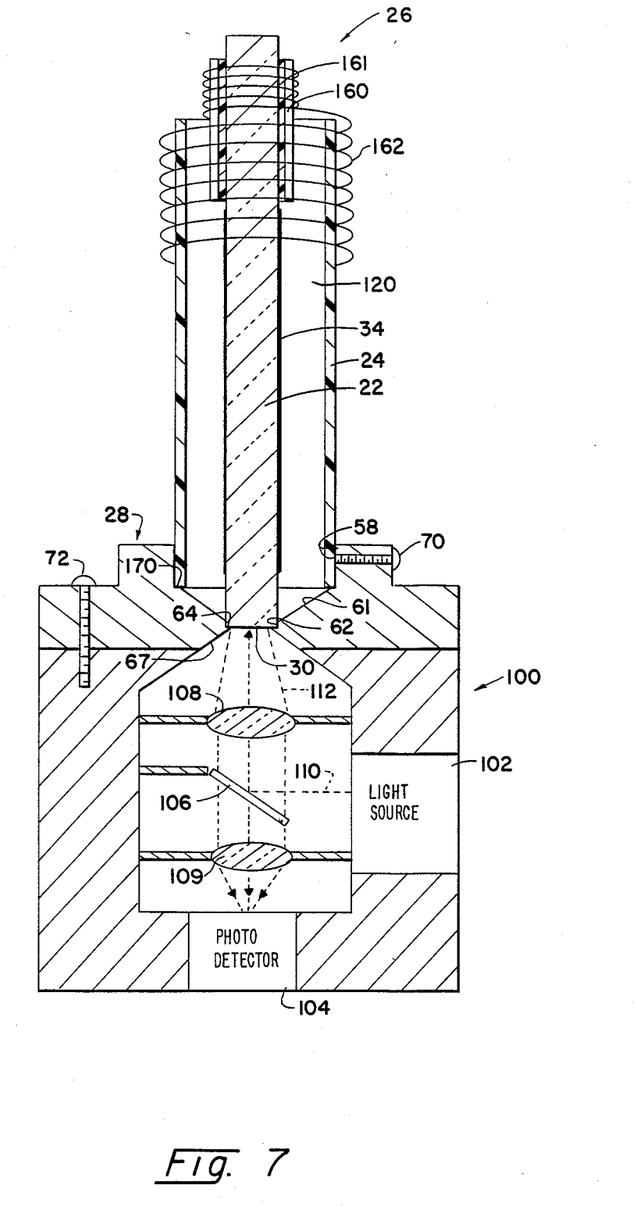
FIG. 7 is an idealized longitudinal cross-sectional view of a fiber optic system embodying the principles of yet another embodiment of the present invention and an optical system with which it is adapted to be used.

An alternate embodiment of the assay apparatus shown in FIG. 5 is illustrated in FIG. 7. The embodiment of FIG. 5 is modified so as to provide the embodiment of FIG. 7 in substantially the same manner the embodiment of FIGS. 1-4 was modified so as to provide the embodiment of FIG. 6, as discussed above. Specifically, seat 170 is provided at the junction of portion 58 and frusto-conically tapering portion 61. As with the embodiment of FIG. 6, seat 170 is designed to provide a fluid-tight seal between the proximal end of tube 24 and base member 28. Alternatively, seat 170 may be defined by a reduced diameter portion (not shown) that is similar to portion 168 in FIG. 6. Optionally, an elastomeric O-ring (not shown) or other suitable means may be provided at seat 170 so as to ensure a fluid-tight seal is achieved between the proximal end of tube 24 and base member 28.

As with the embodiment of FIG. 6, portion 62 (FIG. 7) and seat 64 (FIG. 7) are configured to confront and engage proximal end 30 so as to substantially prevent a fluid sample disposed in tube interspace 120 from leaking past proximal end 30. Fiber centering device 26 is provided to axially bias rod 22 toward seat 64 so as to ensure that proximal end 30 remains engaged with seat 64.

In certain applications, as where the fluid sample is pumped through tube 24 under pressure, it may be desired to seal both ends of the tube. The alternative embodiment illustrated in FIG. 8 is designed to provide this dual-end sealing.

Figure 8:
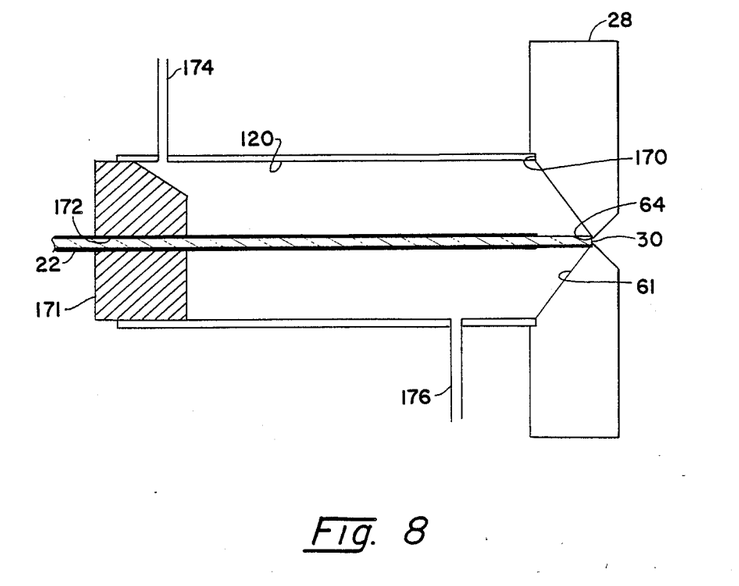
FIG. 8 is an idealized longitudinal cross-sectional view of a fiber optic system embodying the principles of still another embodiment of the present invention and an optical system with which it is adapted to be used.

Base member 28 of the embodiment illustrated in FIG. 8 is substantially identical to the base members 28 of the embodiments illustrated in FIGS. 6 and 7. Specifically, a seat 170 is provided in base member 28 (FIG. 8) to ensure a fluid-tight seal is achieved between tube 24 and the base members. As with the embodiments illustrated in FIGS. 6 and 7, reduced-diameter portion 62 and seat 64 are configured to ensure a substantially fluid-tight seal is achieved between rod 22 and base member 28 when the rod is axially biased to engage portion 64. Insert 171 is provided for fluidly sealing the distal end of tube 24. The latter is sized to engage the inner surface of tube 24 so as to prevent a sample disposed in tube interspace 120 from escaping from the distal end of the tube. Preferably, insert 171 is made from an elastomeric material that is substantially nonreactive with the sample disposed in interspace 120. An aperture 172 is provided in insert 170 for receiving the distal end of rod 22. In the event aperture 172 is formed to extend entirely through insert 171, the diameter of aperture 172 is selected so that insert 171 engages rod 22 so as to substantially prevent a fluid sample disposed in interspace 120 from escaping from the interspace through aperture 172.

Optionally, inlet tube 174 and outlet tube 176 may be provided for fluidly coupling tube interspace 120 to a source (not shown) for providing a fluid assay sample under pressure. Inlet tubes 174 and 176 are connected to tube 24 so as to be fluidly coupled with the interspace 120 thereof. Refering now to FIG. 9, optical system 100 may be modified to include tapered input rod 182. The latter is substantially the same as the tapered fiber transition element shown in FIG. 6 of U.S. Pat. No. 4,654,532 to T.B. Hirschfeld, which patent is incorporated herein by reference. Briefly, tapered rod 182 has a circular cross-section and tapers gradually from relatively large input face 184 to relatively small output face 186. Tapered rod 182 is transmissive to both the excitation and resulting fluorescence radiation, and is preferably made from glass, crystal or plastic. Rod 182 is adapted to propagate along its length by multiple total internal reflection radiation entering either input face 184 or output face 186. As is apparent from U.S. Pat. No. 4,654,532, the taper of tapered fiber 182 preferably should not exceed about 5°.

Figure 9:
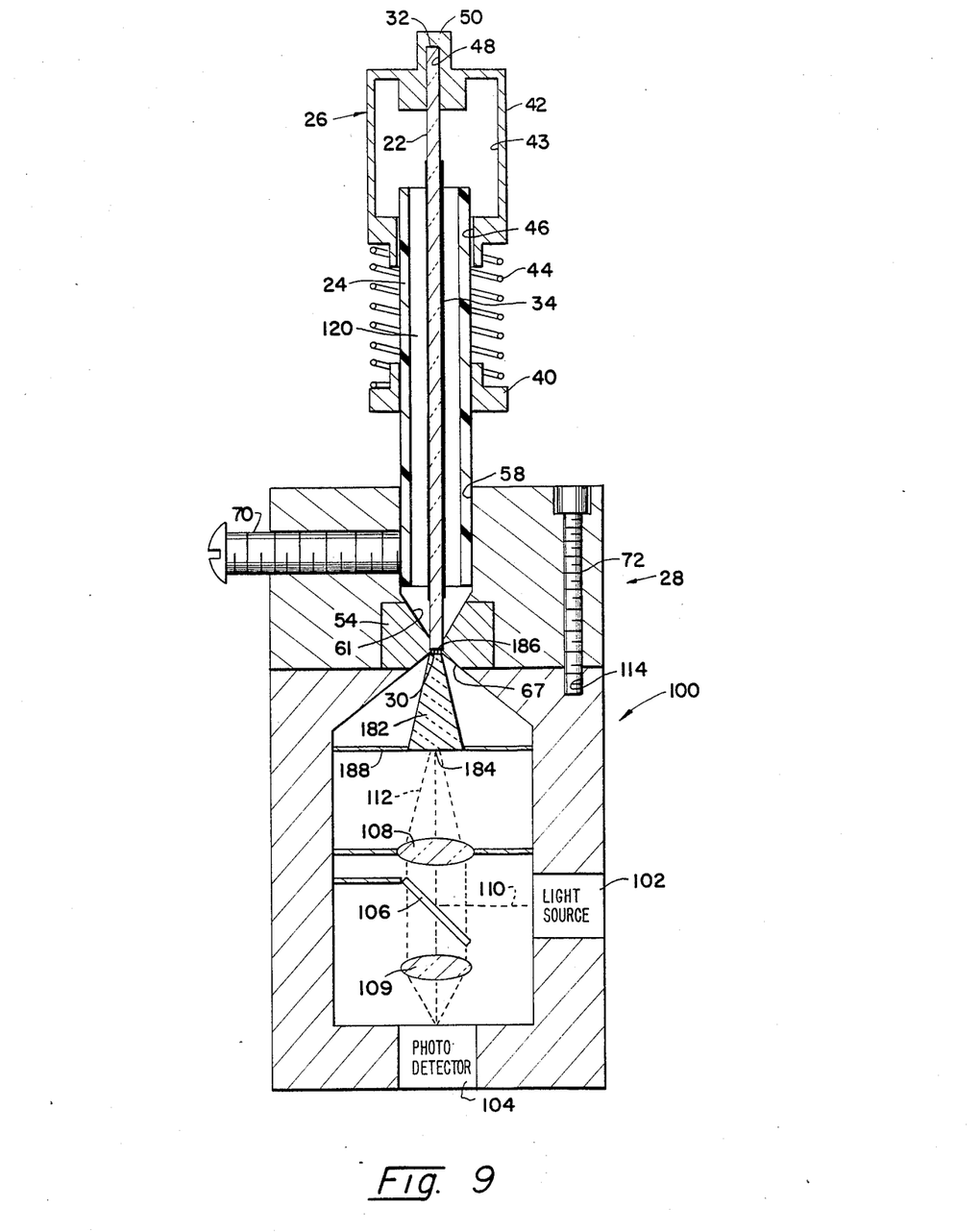
FIG. 9 is an idealized, longitudinal cross-sectional view of the fiber optic system of FIG. 4, including an alternate embodiment of optical system thereof.

Tapered rod 182 is permanently secured to optical system 100 by support 188 so as to be supported in fixed, spaced relation to objective lens 108. Because support 188 limits somewhat the numerical aperture of tapered rod 182 as a result of its contact with the rod, and because the numerical aperture of the rod increases as the latter tapers inwardly toward output face 186, support 188 is secured to the outer surface of tapered rod 182 adjacent input face 184. Preferably, to further minimize limitation in numerical aperture of tapered rod 182, support 188 is made from a transparent material having an index of refraction that is lower than the index of fiber 22, e.g. a material such as siloxane.

The diameter of rod output face 186, is preferably selected so that (a) the peripheral edge of output face 186 contacts frusto-conical portion 67 adjacent seat 64 and (b) output face 186 is spaced a selected distance, e.g. typically 0.005 to 0.050 inches, from fiber proximal end 30. Substantially no input radiation is lost by this contact because by spacing output face 186 from proximal end 30 in the manner discussed above, the light rays emitted from output face 186 adjacent the peripheral edge thereof exit the output face at an angle such that these rays will intersect proximal end 30, and not portions of frusto-conical portion 67 adjacent the proximal end. The length of tapered rod 182 is selected so that when output face 186 is spaced from proximal end 30 as noted above, rod input face 184 is positioned approximately at the focus of objective lens 108.

As described in detail in the aforementioned U.S. Pat. No. 4,654,532, the numerical aperture of tapered rod 182 increases as the rod tapers toward output face 186 by an amount proportional to the ratio of the area of output face 186 and the cross section of the rod at any selected point along the length of the rod. As a result of this increase in numerical aperture, input lenses of lower numerical aperture may be used in optical system 100. Such lower numerical aperture lenses are cheaper, easier to build, better corrected, tend to have higher transmission, and also have better depths of field so that focusing them is less critical.

Several other important advantages are achieved by using tapered rod 182 in optical system 100. First, because it is difficult to provide multiple reproduction of the exact taper of tapered rod 182 within reasonable tolerance limits, such tapered rods are not practical consumable components of the assembly which includes rod 22 and enclosure 24. Because of this variation in reproduceability of the taper, if tapered rods 182 are included in the consumable assembly it would be necessary to recalibrate the optical system of the assay apparatus to compensate for each taper variant before each assay to maintain sufficient apparatus accuracy. This recalibration would be both time-consuming and expensive. Consequently, by permanently mounting tapered rod 182 in optical system 100, the aforementioned problems arising from variation in taper of the rod are eliminated and the apparatus need only be factory calibrated for the specific rod 182 used therein. Cylindrical rod 22, of course, being manufacturable within sufficiently narrow tolerances at relatively low cost, does not introduce variations necessitating recalibration of the assay apparatus. Secondly, during the manufacture of optical system 100 it is relatively easy to obtain accurate positioning of tapered rod 182 therein, as frusto-conical portion 67 serves to automatically align the rod relative to seat 64 upon insertion of rod 182 into portion 67. Additionally, frusto-conical portion 67 coacts with the output face end of rod 182 so as to provide a substantially water-tight seal between rod 182 and portion 67 when rod is supported by support 188 to engage portion 67.

Since certain changes may be made in the above process and apparatus without departing from the scope of the invention herein involved, it is intended that all matter contained in the above description or shown in the accompanying drawing shall be interpreted in an illustrative and not in a limiting sense.

What is claimed is:

1. In apparatus for assaying a fluid sample and including a totally internally reflecting, elongated, substrate transmissive to excitation radiation directed at a proximal end of said substrate by an optical system; which radiation, when propagated through said substrate, will provide an evanescent wave for exciting fluorescence in fluorescent material disposed at least on a portion of the surface of said substrate, said substrate also being transmissive to said fluorescence; and a hollow elongated enclosure spaced from and surrounding the surface of said substrate, the improvement comprising:

mounting means couplable to said optical system and to said substrate and to said enclosure for mounting said substrate within said enclosure, said mounting means comprising:

seat means spaced a fixed predetermined distance from said optical system when said mounting means is coupled to said optical system, for so releasably seating said proximal end in a preselected position fixed at least axially with respect to the long axis of said substrate and with respect to said optical system, that when said proximal end is seated in said seat means, substantially all of said excitation radiation entering said proximal end from said optical system at a solid angle less than or equal to a maximum acceptance angle determined in part by the refractive index of said sample, undergoes total internal reflection within said substrate.

2. In apparatus as defined in claim 1, wherein said mounting means imposed substantially no restriction on said maximum acceptance angle.

3. In apparatus as defined in claim 1, wherein said mounting means comprises a base member having a frusto-conically tapering aperture formed therein, and bore and counterbore means for holding said proximal end of said substrate so that said substrate (a) is substantially prevented from moving transversely of its axial dimension with respect to said base member and (b) is prevented from moving in a first direction along its axial dimension with respect to said base member, said bore means extends through said base member in coaxial alignment with said frusto-conically tapering aperture so as to intersect an apex end of said aperture, and said counterbore means is coupled with and coaxially aligned with said bore means and is coupled with the apex end of said frusto-conically tapering aperture.

4. In apparatus as defined in claim 3, wherein said seat means is provided in said counterbore means for supporting a peripheral portion of said proximal end of said substrate so as to prevent said substrate from moving in said first axial direction with respect to said base member and so that a fixed spatial relationship is maintainable between said proximal end and said radiation source.

5. In apparatus as defined in claim 3, said base member comprising enclosure aperture means for receiving said elongated enclosure so as to substantially prevent said elongated enclosure from moving transversely of its axial dimension.

6. In apparatus as defined in claim 5, wherein said base member comprises quick-release clamp means for releasably securing said elongated enclosure in said enclosure aperture means so that said elongated enclosure can be easily secured to and removed from said base member and so that said elongated enclosure is prevented from moving along its axial dimension when secured to said base.

7. In apparatus as defined in claim 3, said mounting means comprising biasing means for urging said elongated substrate in said first axial direction.

8. In apparatus as defined in claim 1, wherein said mounting means is coupled to a distal end of said elongated means and comprises an opening adjacent said distal end through which a fluid sample may be introduced into said enclosure.

9. In apparatus as defined in claim 1, wherein said mounting means comprises a hollow body secured to a distal end of said substrate, said hollow body comprising aperture means for slidably receiving a distal end of said elongated enclosure so that said distal end of said substrate and said hollow body are substantially prevented from moving transversely relative to said distal end of said elongated enclosure, said hollow body comprising an opening through which a fluid sample may be introduced into said elongated enclosure.

10. In apparatus as defined in claim 9, said mounting means comprising biasing means surrounding said elongated enclosure having a first end attached to said hollow body and a second end attached to said elongated enclosure for urging said substrate in a first axial direction with respect to said elongated enclosure.

11. In apparatus as defined in claim 1, said mounting means comprising spacer means secured to said substrate adjacent a distal end of said substrate and extending into said elongated enclosure adjacent a distal end of said enclosure for substantially preventing said distal end of said substrate from moving transversely relative to said enclosure, said spacer means being sized so that a gap exists between said spacer means and said enclosure through which a fluid sample may be introduced into said enclosure.

12. In apparatus as defined in claim 11, said mounting means comprising biasing means surrounding said elongated enclosure and having a first end attached to said spacer means and a second end attached to said elongated enclosure for urging said substrate in a first axial direction with respect to said elongated enclosure.

13. In apparatus for assaying a fluid sample and including a totally internally reflecting elongated substrate transmissive to radiation capable of providing an evanescent wave for exciting fluorescence in fluorescent material disposed at leas on a portion of the surface of said substrate, said substrate also being transmissive to said fluorescence, and elongated means spaced from said surface of said substrate so as to define a hollow elongated enclosure surrounding said surface, and optical means couplable to said mounting means for transmitting a beam of optical radiation to an end face of said substrate, the improvement comprising:

means coupled to said substrate and said elongated means for mounting said substrate within said enclosure and for releasably supporting both ends of said elongated substrate so that said end face is axially positionable at a fixed location with respect to said optical means and so that said elongated substrate is (a) substantially prevented from moving transversely relative to its longitudinal axis and (b) is prevented from moving in a first axial direction relative to said optical means.

14. In apparatus as defined in claim 13, said optical means further comprising light source means for transmitting said radiation so as to enter said substrate at said end face at a solid angle less than or equal to the maximum acceptance angle determined in part by the refractive index of said sample, and photo-detector means for detecting said fluorescence transmitted through said end face.

15. In apparatus as defined in claim 14, said mounting means comprising seat means for supporting a peripheral portion of said end face so as to achieve substantially total internal reflection of said radiation which is transmitted into and is emitted from said elongated substrate.

16. In apparatus as defined in claim 15, wherein said seat means is positioned at a location that is spaced a discrete distance from said optical means.

17. In apparatus as defined in claim 15, said mounting means comprising biasing means coupled to said substrate and said elongated means for biasing said end face in said first direction against said seat means.

18. In apparatus as defined in claim 17, wherein said biasing means comprises a coil spring surrounding said elongated substrate and said elongated means, said coil spring having a first end secured to said elongated substrate and a second end secured to said elongated means.

19. In apparatus as defined in claim 15, said supporting means comprising centering means for cooperating with said end face so as to cause said end face to move radially and axially toward said seat upon insertion of said substrate into said supporting means.

20. In apparatus as defined in claim 13 wherein said optical means comprises an objective lens system.

21. In apparatus as defined in claim 13 wherein said supporting means cooperates with said elongated substrate to hold the latter in coaxial alignment in said enclosure.

22. In apparatus as defined in claim 13 wherein said substrate is an optical rod having a circular cross-section and a substantially uniform diameter.

23. In apparatus for assaying a fluid sample and including a totally internally reflecting, elongated, substrate transmissive to excitation radiation from a radiation source, which radiation is capable of providing an evanescent wave for exciting fluorescence in fluorescent material disposed at least on a portion of the surface of said substrate, said substrate also being transmissive to said fluorescence, said substrate comprising a proximal end through which said excitation radiation and excited fluorescence may be transmitted, a hollow elongated enclosure spaced from and surrounding the surface of said substrate, the improvement comprising:
mounting means couplable to said substrate and to said enclosure for mounting said substrate within said enclosure, said mounting means comprising:
means defining a fixed interface between said mounting means and said radiation source;
seat means for supporting said proximal end in a preselected position with respect to said interface, so that substantially all of said excitation radiation entering said proximal end at a solid angle less than or equal to a maximum acceptance angle determined in part by the refractive index of said sample undergoes total internal reflection within said substrate; and
seal means for creating a barrier past which a fluid sample disposed within said enclosure cannot escape.

24. In apparatus according to claim 23, wherein said seal means is disposed adjacent both a distal and said proximal end of said enclosure so as to prevent said fluid sample from escaping from either said distal or proximal ends of said enclosure past said barrier.

25. In apparatus according to claim 23, wherein said seal means is disposed adjacent said proximal end of said enclosure so as to prevent said fluid sample from escaping from said proximal end of said enclosure past said barrier.

26. In apparatus according to claim 23, wherein said mounting means comprises a base member for receiving a proximal end of said enclosure and said proximal end of said substrate, further wherein said seal means comprises lip means provided in said base member for engaging said proximal end of said enclosure and said proximal end of said substrate so as to define a barrier past which a fluid sample disposed within said enclosure cannot escape.

27. In apparatus according to claim 26, said seal means further comprising O-ring means disposed adjacent said lip means for ensuring a fluid-tight seal is achieved between (1) said proximal end of said enclosure and said proximal end of said substrate and (2) said base member.

28. In apparatus as defined in claim 1 including means associated with the distal end of said substrate for absorbing said excitation radiation.

29. In apparatus as defined in claim 28 wherein said means for absorbing has an index of refraction substantially matched to the index of refraction of the medium immediately surrounding said distal end.

30. In apparatus for assaying a fluid sample and including a totally internally reflecting elongated substrate transmissive to radiation capable of providing an evanescent wave for exciting fluorescence in fluorescent material disposed at least on a portion of the surface of said substrate, said substrate also being transmissive to said fluorescence, and elongated means spaced from said surface of said substrate so as to define a hollow elongated enclosure surrounding said surface, and optical means couplable to said mounting means for transmitting a beam of optical radiation to an end face of said substrate, the improvement comprising:
means coupled to said substrate and said elongated means for mounting said substrate within said enclosure and for releasably supporting both ends of said elongated substrate so that said end face is axially positionable at a fixed location with respect to said optical means and so that said elongated substrate is (a) substantially prevented from moving transversely relative to its longitudinal axis and (b) is prevented from moving in a first axial direction relative to said optical means; and
wherein said optical means comprises a tapered fiber disposed in fixed spatial relationship relative to said fiber end face, said tapered fiber having an input face and an output face, said tapered fiber being transmissive to said optical radiation and being tapered smoothly so as to reduce the diameter of said tapered fiber from said input face to said output face.

31. In apparatus according to claim 30, wherein said optical means comprises an optical element and wherein said input face is disposed adjacent said optical element and said output face is disposed adjacent said fiber end face.

32. Apparatus as defined in claim 1 wherein said seat means substantially prevents movement of said proximal end radially with respect to the long axis of said substrate when said proximal end is seated in said seat means.

* * * * *

UNITED STATES PATENT AND TRADEMARK OFFICE
CERTIFICATE OF CORRECTION

PATENT NO. : 4,909,990

DATED : March 20, 1990

INVENTOR(S) : Myron J. Block, et al.

It is certified that error appears in the above-identified patent and that said Letters Patent is hereby corrected as shown below:

Claim 2, column 15, line 30, delete "imposed" and substitute therefor -- imposes --; and Claim 13, column 16, line 45, delete "leas" and substitute therefor -- least --.

Signed and Sealed this

Twenty-first Day of May, 1991

*Attest:*

HARRY F. MANBECK, JR.

*Attesting Officer*   *Commissioner of Patents and Trademarks*